(12) United States Patent
Tsai et al.

(10) Patent No.: US 8,753,904 B2
(45) Date of Patent: Jun. 17, 2014

(54) METHOD AND SYSTEM FOR SEMICONDUCTOR DEVICE PATTERN LOADING EFFECT CHARACTERIZATION

(75) Inventors: Chun Hsiung Tsai, Xinpu Township, Hsinchu County (TW); Sheng-Wen Yu, New Taipei (TW); De-Wei Yu, Ping-Tung (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/491,252

(22) Filed: Jun. 7, 2012

(65) Prior Publication Data
US 2013/0330847 A1   Dec. 12, 2013

(51) Int. Cl.
*H01L 21/00* (2006.01)

(52) U.S. Cl.
USPC .................. 438/16; 438/14; 257/E21.001

(58) Field of Classification Search
USPC ........................................................ 438/16
See application file for complete search history.

(56) References Cited

U.S. PATENT DOCUMENTS

| | | | | |
|---|---|---|---|---|
| 5,561,088 A * | 10/1996 | Sameshima | ................... | 438/166 |
| 6,333,485 B1 * | 12/2001 | Haight et al. | ............ | 219/121.68 |
| 6,403,396 B1 * | 6/2002 | Gudesen et al. | ................. | 438/99 |
| 6,432,739 B1 * | 8/2002 | Gudesen et al. | ................. | 438/99 |
| 6,656,749 B1 * | 12/2003 | Paton et al. | ....................... | 438/5 |
| 6,727,108 B2 * | 4/2004 | Eriguchi et al. | ................ | 438/16 |
| 6,776,806 B2 * | 8/2004 | Gudesen et al. | .............. | 29/25.01 |
| 7,098,155 B2 * | 8/2006 | Talwar et al. | .................. | 438/795 |
| 7,148,159 B2 * | 12/2006 | Talwar et al. | .................. | 438/795 |
| 7,262,864 B1 * | 8/2007 | Markle et al. | .................. | 356/625 |
| 7,348,192 B2 * | 3/2008 | Mikami | ........................... | 438/16 |
| 7,494,942 B2 * | 2/2009 | Talwar et al. | .................. | 438/795 |
| 7,623,978 B2 * | 11/2009 | Lally et al. | ....................... | 702/81 |
| 7,820,531 B2 * | 10/2010 | Matsunobu et al. | .......... | 438/487 |
| 7,879,741 B2 * | 2/2011 | Talwar et al. | .................. | 438/795 |
| 7,935,585 B2 * | 5/2011 | Sato et al. | ....................... | 438/166 |
| 8,232,114 B2 * | 7/2012 | Lin et al. | ......................... | 438/16 |
| 2005/0112788 A1 * | 5/2005 | Borden et al. | ................... | 438/14 |
| 2005/0200850 A1 * | 9/2005 | Borden et al. | ................. | 356/432 |
| 2007/0020784 A1 * | 1/2007 | Timans | .......................... | 438/16 |
| 2007/0105247 A1 * | 5/2007 | Mauersberger et al. | ......... | 438/16 |
| 2010/0190274 A1 | 7/2010 | Lin et al. | | |
| 2012/0015459 A1 | 1/2012 | Tsai et al. | | |
| 2012/0021539 A1 * | 1/2012 | Allenic et al. | ..................... | 438/7 |

OTHER PUBLICATIONS

P.J. Timans; "A Short History of Pattern Effects in Thermal Processing / Rapid Thermal Processing and Beyond: Applications in Semiconductor Processing;" Materials Science Forum vols. 573-574 (Mar. 24, 2008), pp. 355-374, www.scientific.net.

* cited by examiner

*Primary Examiner* — Scott B Geyer
*Assistant Examiner* — Evren Seven
(74) *Attorney, Agent, or Firm* — Haynes and Boone, LLP

(57) ABSTRACT

The present disclosure provides a method and system for characterizing a pattern loading effect. A method may include performing a reflectivity measurement on a semiconductor wafer and determining an anneal process technique based on the reflectivity measurement. The determining the anneal process technique may include determining a spatial distance for a reflectivity change using a reflectivity map generated using the reflectivity measurement. This spatial distance is compared with the thermal diffusion length associated with each of the plurality of anneal process techniques. In an embodiment, a thermal profile map and/or a device performance map may be provided.

20 Claims, 5 Drawing Sheets

METHOD AND SYSTEM FOR SEMICONDUCTOR DEVICE PATTERN LOADING EFFECT CHARACTERIZATION

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process has decreased. This scaling down process generally provides benefits by increasing production efficiency and lowering associated costs. Such scaling down has also increased the complexity of processing and manufacturing ICs and, for these advances to be realized, similar developments in IC processing and manufacturing are needed.

One IC process typically performed during semiconductor device fabrication is an anneal. For example, an anneal may be used to drive-in dopants to provide a suitable dopant profile. One challenge with the increasing complexity of semiconductor devices is the presence of a loading effect, also referred to as a pattern loading effect (PLE) during an anneal process. The pattern loading effect phenomenon derives from differences in radiant energy absorption in different areas of a semiconductor device or die on account of the different patterning (e.g., pattern density, aspect ratio of features, composition/reflectivity of features, etc.). In conventional processing the effects on semiconductor device performance from the PLE is characterized during electrical test. This has its disadvantages in efficiency and effectiveness of the characterization.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
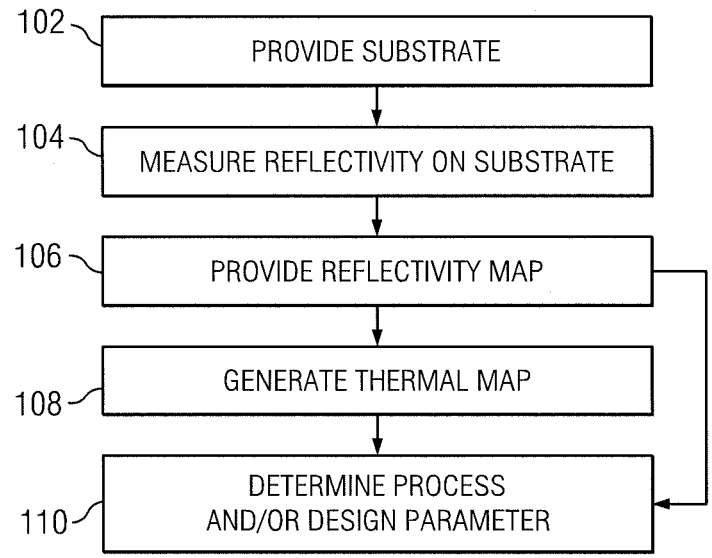
FIG. 1 is a flow chart illustrating an embodiment of a method of characterization according to one or more aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for simplicity and clarity. The term characterization as used herein includes, but is not limited to, an analysis of a semiconductor device, semiconductor device design, the analysis and/or determination of various process parameters, analysis and/or determination of design elements or layout, disposition of material (e.g., product, device, wafer, lot), analysis and/or determination of process technique to be used, and/or other functions.

During semiconductor device fabrication, a thin layer of semiconductor material may be doped to alter the electrical characteristics of the material. Generally, doping is the process of implanting ions into the semiconductor material and may be performed by an ion implant process wherein the semiconductor layer is bombarded with N-type and/or P-type ions or by an in situ process wherein ions are introduced as the semiconductor layer is being formed.

After the doping process, an annealing process is typically performed to activate the implanted ions (e.g., N-type and/or P-type ions). When performing the annealing procedure, however, it has been found that the individual dies of a wafer may not heat evenly, or specifically a different amount of heat may be absorbed at different regions of a die and/or wafer. In some embodiments, the die may exhibit a significant amount of temperature variation across the die. The variations in heat absorbed may stem from differences in doping level, pattern density, pattern configuration, pattern aspect ratio, reflectivity of layers, and/or other variations across a die. This is referred to herein as a pattern loading effect (PLE).

This pattern loading effect and resultant temperature differences may result in the various semiconductor devices, e.g., transistors, resistors, capacitors, and the like, on the same die to exhibit different electrical characteristics. For example, when a first region, e.g., edges of a die, are heated to a significantly lower temperature than a second region, e.g., the center of the die, the dopants in the second region may not be sufficiently activated resulting in increased resistance and greater circuit delays as compared to the first region. As a result, the various semiconductor devices or portions of the IC may have different electrical characteristics based upon the position on the die.

Referring now to FIG. 1, illustrated is a method 100 of characterizing a wafer and/or die including determining a pattern loading effect. The method 100 may be used to determine, for a given wafer, die or design—a device performance parameter, a suitable process technique for its fabrication, and/or a determination of the suitability of a layout provided on the wafer or die.

The method 100 begins at block 102 where a substrate is provided. In an embodiment, the substrate is a semiconductor wafer. The wafer may be a silicon wafer. The substrate may also include other elementary semiconductors such as germanium and diamond. Alternatively, the substrate may include a compound semiconductor and/or an alloy semiconductor. Further, the substrate may optionally include an epitaxial layer (epi layer), may be strained for performance enhancement, may include a silicon-on-insulator (SOI) structure, and/or have other suitable enhancement features. The wafer may include a plurality of die formed thereon.

The die may include any number of semiconductor devices, such as field effect transistors (FETs), capacitors, resistors, conductive interconnects, and/or other suitable devices. The die may include various doped regions or regions of the substrate (including layers on semiconductor wafer) with suitable N-type or P-type dopants (impurities). Exemplary regions include active regions on which MOS devices can be formed; the active regions may be doped to form well regions. The doped regions, including but not limited to active regions, may vary in dimension, dopant level, configuration, and/or other properties. The boundaries of the active regions may be defined by isolation structures such as shallow trench isolation (STI) features.

The die may also include any plurality of layers formed on a base substrate including conductive layers, insulating layers, masking layers, antireflective coatings, etch stop layers, gate layers, interconnection layers, and/or other features. These layers may form features (e.g., gate structures, conductive capacitor plates, interconnect lines, source/drain regions, isolation regions) of varying dimensions (e.g., height and widths). These layers may also form regions on the die having different pattern densities.

Figure 2:
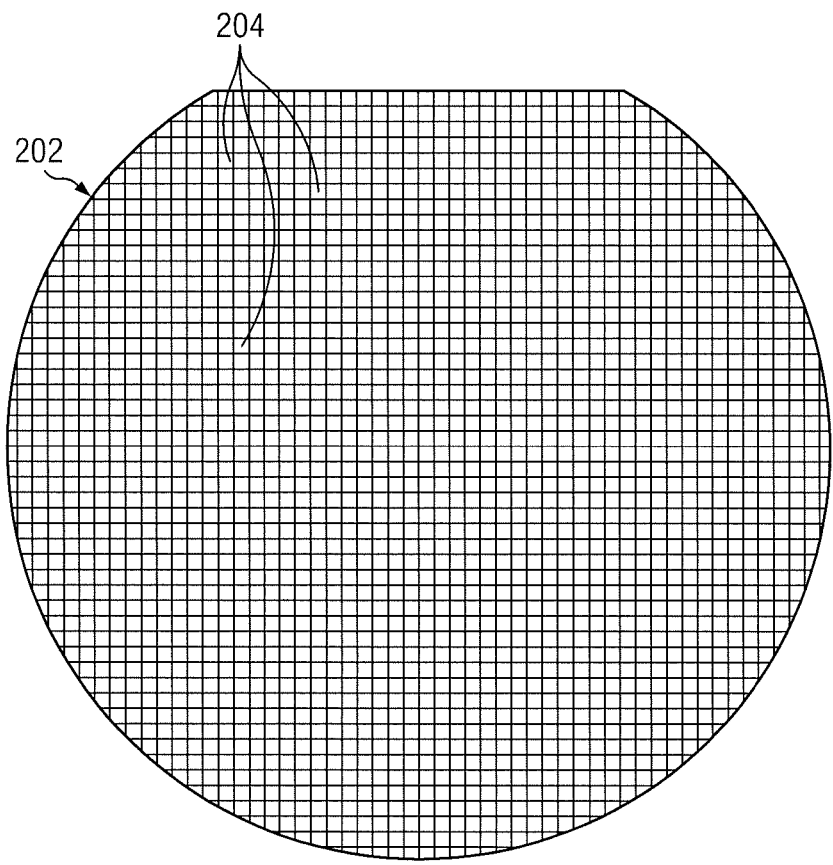
FIG. 2 is a top view of an embodiment of a wafer.

In an embodiment, the dies may be representative of a single semiconductor device product. In another embodiment, the dies may be used to form any number of different semiconductor device products. In other words, the dies of a wafer may be associated with different designs or a common design. For example, a first plurality of dies of the wafer may be a first semiconductor device product or have a first design; a second plurality of dies on the same wafer may be a second semiconductor device product or have a second design. Referring to the example of FIG. 2, a wafer 202 is illustrated having a plurality of dies 204. One or more die 204 of the wafer 202 may have a different intra-die pattern loading effect. In other embodiments, one or more die 204 exhibit a substantially similar intra-die pattern loading effect.

The method 100 then proceeds to block 104 where a reflectivity is measured for the substrate. The reflectivity of the substrate, and/or a die formed thereon, may be dependent upon the materials present, the pattern density of the devices, e.g., transistors, resistors, capacitors, and/or other suitable factors. The reflectivity measured includes the amount (e.g., intensity) of radiation (light) reflected from a radiation beam incident the substrate.

In an embodiment, the reflectivity measurement of the substrate is performed using a radiation source that has a relativity short wavelength such as, for example, a source providing a radiation beam having a wavelength between approximately 200 nanometers (nm) and approximately 750 nm. Thus, in an embodiment, a flash Xeon lamp is used as a light source. In an embodiment, the main distribution of the wavelength of the radiation (e.g., light) source is between approximately 300 nm and approximately 500 nm. This may provide a wavelength distribution of reflectivity measurement that covers the wavelength distribution of a radiation/light source, which is actually experienced by the substrate during an anneal process. The reflectivity measurement may include a scan of the substrate. The scan may be a full-wafer scan, or a scan of a representative sample of regions (e.g., die) on the device. In an embodiment, a spot size of approximately 3 μm is used for the scan. In a further embodiment, a stepping distance of approximately 50 μm or greater is used. These scan parameters are by way of example only. The reflectivity measurement or scan may provide a two-dimensional reflectivity map corresponding to the substrate. The reflectivity map may include a reflectivity measurement for one or more points on the substrate.

Figure 3:
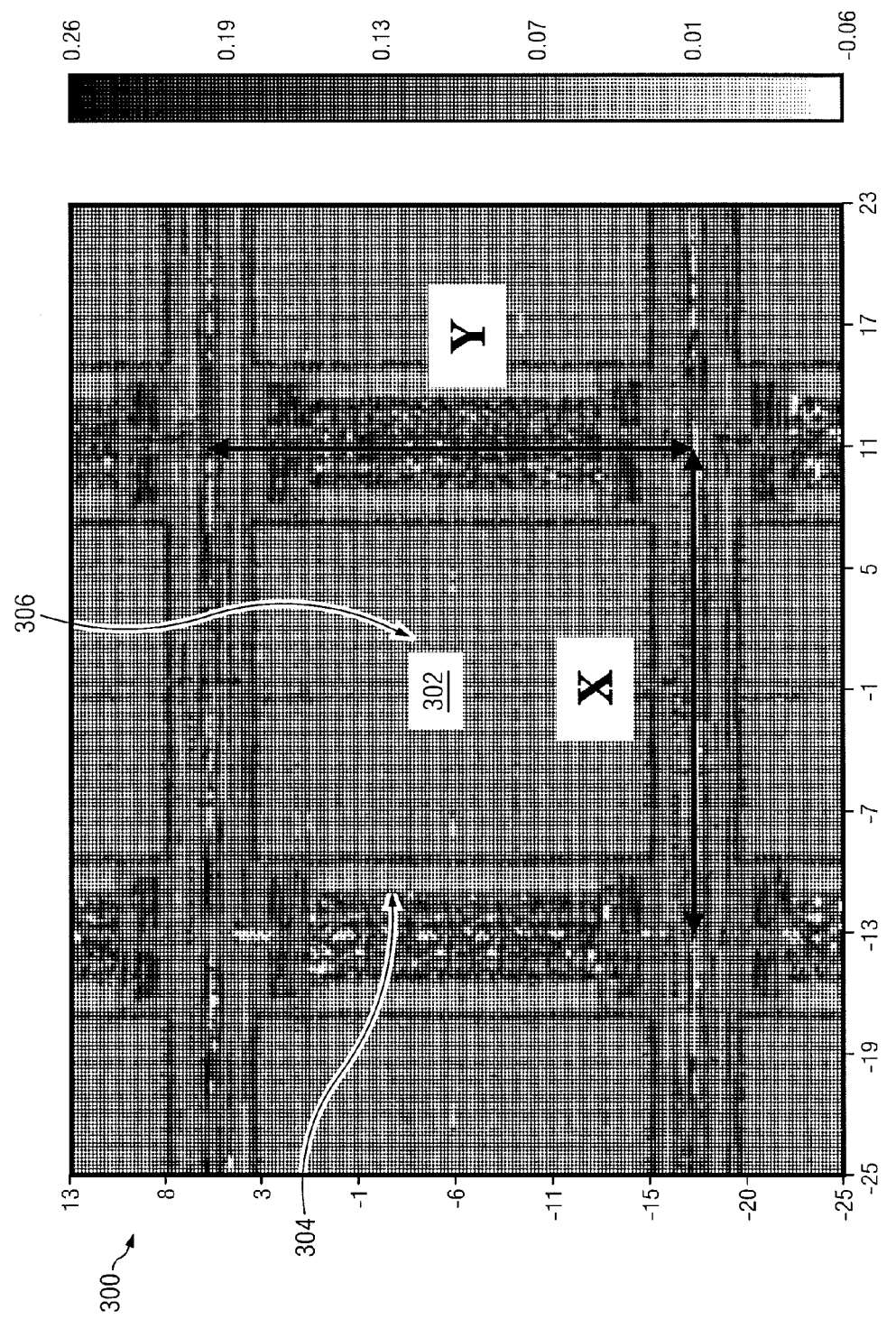
FIG. 3 is an embodiment of a reflectivity map such as generated during one or more steps of the method of FIG. 1.

An exemplary reflectivity map 300 is illustrated in FIG. 3. Though the reflectivity map 300 illustrates a portion of a wafer (e.g., approximately 9 die), any size of area may be used in the scan and/or provided in the reflectivity map. In an embodiment, the reflectivity map is representative of an entire substrate. In another embodiment, the reflectivity map is representative of one or more die on the substrate (e.g., map 300).

The reflectivity map 300 illustrates a plurality of dies including die 302. Die 302 has a dimension of X and Y. In an embodiment, X and Y may be approximately 2 centimeters (cm). However, any dimension is possible. In fact, one advantage of various embodiments of the present disclosure is that it can be used for any technology node or any sized/configuration of die. The reflectivity map 300 includes a value of intensity of a reflected radiation beam determined for a given point (or points) on a substrate. The reflectivity map 300 illustrates the die 302 has a relatively higher reflectivity at the edge-region 304 and a relatively lower reflectivity at the center-region 306. The reflectivity scale of the map 300 includes a low reflectivity (e.g., 0, 0.01) to higher relative reflectivity (e.g., 0.26).

In an embodiment, the method 100 proceeds to block 110 where the reflectivity map may be analyzed to determine a process parameter including, for example, determining a specific anneal technique to implement as described in further detail below, determining a device performance parameter (e.g., leakage, speed, etc including as described below with reference to a device performance parameter map), performing an evaluation of an associated design or layout (e.g., a determination of whether a modification layout to a design or layout is desired as described below), and/or other suitable characterization. Each of these characterizations is described in further detail below.

It is noted that reflectivity variation over a region (e.g., die) is an indication of the temperature variations over the same region. For example, there may be an inverse relationship between reflectivity and temperature: regions exhibiting a higher reflectivity are lower in temperature in comparison to regions exhibiting lower reflectivity. The reflectivity map may be used to predict device performance including intra- and/or inter-die variation. As described below, the analysis of the reflectivity map may be used to determine a configuration for an anneal process. The higher the reflectivity, the greater the amount of the radiation energy of the heat source of the anneal may be reflected during the anneal process. Thus, an appropriate anneal that allows for the pattern loading effect to be acceptable (within a given tolerance or margin) may be determined from the reflectivity map. An appropriate anneal may be one that may be performed without design modification to improve a PLE. In some embodiments, the analysis of the reflectivity map may additionally or alternatively provide for a disposition of the design of a die (e.g., layout), a modification of the design of the die, a selection of an anneal process parameter, a determination of a performance parameter for the device, and/or other suitable characterization. These analysis are described in greater detail below.

In an embodiment, the method 100 proceeds to block 108 where a thermal map is generated from the reflectivity map.

The reflectivity map may be converted to a two-dimensional thermal map. By conducting an anneal of various blanket substrates (e.g., wafers) coating with films of individual and/or varying reflectivity (e.g., silicon nitride or an anti-reflective film), various temperatures can be detected on individual blanket wafers by inputting the same thermal budget. Therefore, the correlation between reflectivity and temperature can be determined. Thus, providing information for the reflectivity map to be converted into a thermal map.

Generally, in some embodiments, the thermal map may be generated using a model, experimental data, and/or other analysis techniques. For example, in an embodiment, a given percentage change in reflectivity provides a given temperature variation (e.g., as determined by a model). For example, a 10% reflectivity difference may provide an approximate 100 C variation. Thus, the reflectivity map may illustrate a reflectivity difference over a given distance of the substrate that can be correlated to provide a thermal map a region corresponding to that of the reflectivity map. The thermal map may be used to predict device performance including intra- and/or inter-die variation. For example, see the description directed to FIG. 4 below. The analysis of the thermal map may provide for a disposition of the design of a die (e.g., layout), a modification of the design of the die, a selection of an anneal process, a selection of an anneal process parameter, a determination of a performance parameter for the device, and/or other suitable characterization.

Figure 4:
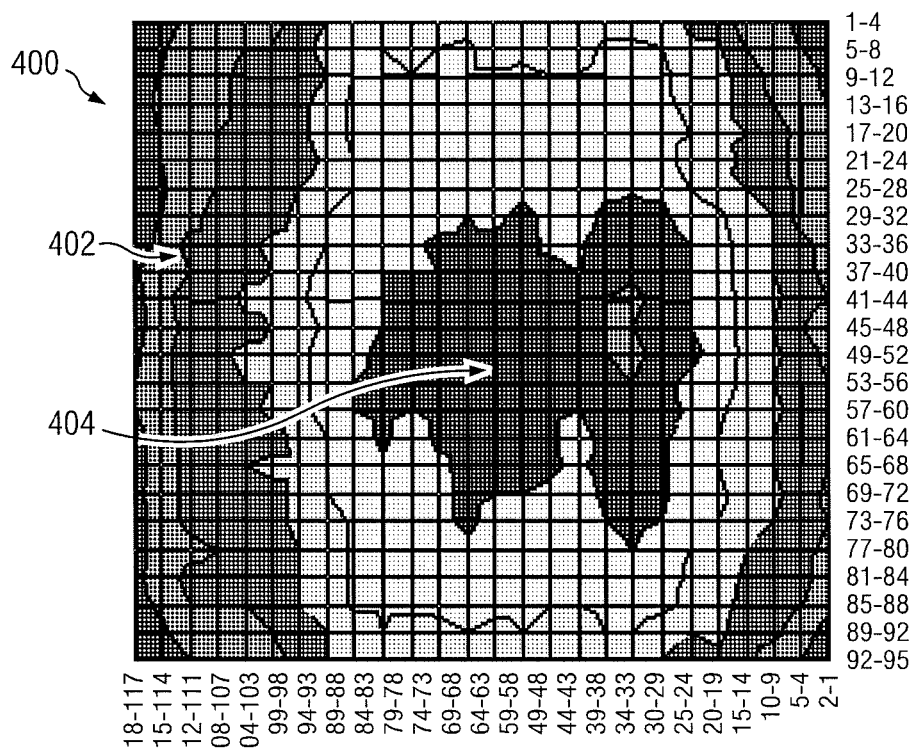
FIG. 4 is an embodiment of a thermal map such as generated during one or more steps of embodiments of the method of FIG. 1.

Referring to the example of FIG. 4, illustrated is a thermal map 400. The thermal map 400 illustrates a center region 404 and an edge region 402. The map 400 has a center-hot, edge-cool temperature profile. In an embodiment, a thermal map is generated having corresponding regions to an associated reflectivity map. In another embodiment, a one-to-one correlation between a thermal map and an associated reflectivity map is not required. For example, a correlation or model used to generate the thermal map may extrapolate one or more points, may have a reduction in the number of points calculated, may be over a reduced or increased area of a wafer, and/or other variations. In an embodiment, this center-hot, edge-cool temperature corresponds to a reflectivity map having a low reflectivity-center region and a high-reflectivity edge region (e.g., the reflectivity map 300). For example, the temperature and reflectivity are inversely related. The thermal map may include a thermal value at any number of points on a substrate or portion thereof.

The method 100 then proceeds to block 110 where a process, design, and/or device performance parameter is determined. The process, design, and/or device performance parameters may be determined using at least one of the reflectivity map, discussed above with reference to block 106 and the thermal map, discussed above with reference to block 108.

In an embodiment, a process parameter associated with the wafer is determined. The process parameter may be determined using the reflectivity measurement, the reflectivity map, and/or the thermal map. The process parameter may be a type of anneal technique to be performed, a duration of an anneal, a temperature of an anneal, and/or other suitable process parameters. In an embodiment, a determination of the process parameter includes determining a type of high temperature technique to perform, such as, for example, a rapid thermal anneal (RTA) (e.g., second RTA spike anneal), a millisecond anneal (mSA), a solid phase epitaxial regrowth (SPER), a flash anneal, a single-step anneal (SSA), a microsecond anneal (uSSA), a flash lamp anneal (FLA), and/or other suitable anneal process.

The determination of the process parameter (e.g., type of anneal) may be performed by determining a spatial distance for a given reflectivity change. This spatial distance is then compared to the thermal diffusion length of one or more of the anneal process techniques. This comparison yields a determination if, for the given anneal, a pattern loading effect solution is desired to avoid and/or mitigate PLE. In an embodiment, for one or more of the anneal techniques, the respective thermal diffusion length is greater than the spatial distance for the given reflectivity change. Thus, the one or more anneal techniques that have a greater thermal diffusion length can be implemented in the process without a PLE solution (e.g., that anneal technique may be performed without accounting or otherwise correcting for PLE). In an embodiment, the given reflectivity change used to determine the spatial distance is approximately 0.1 or 10%.

Figure 6:
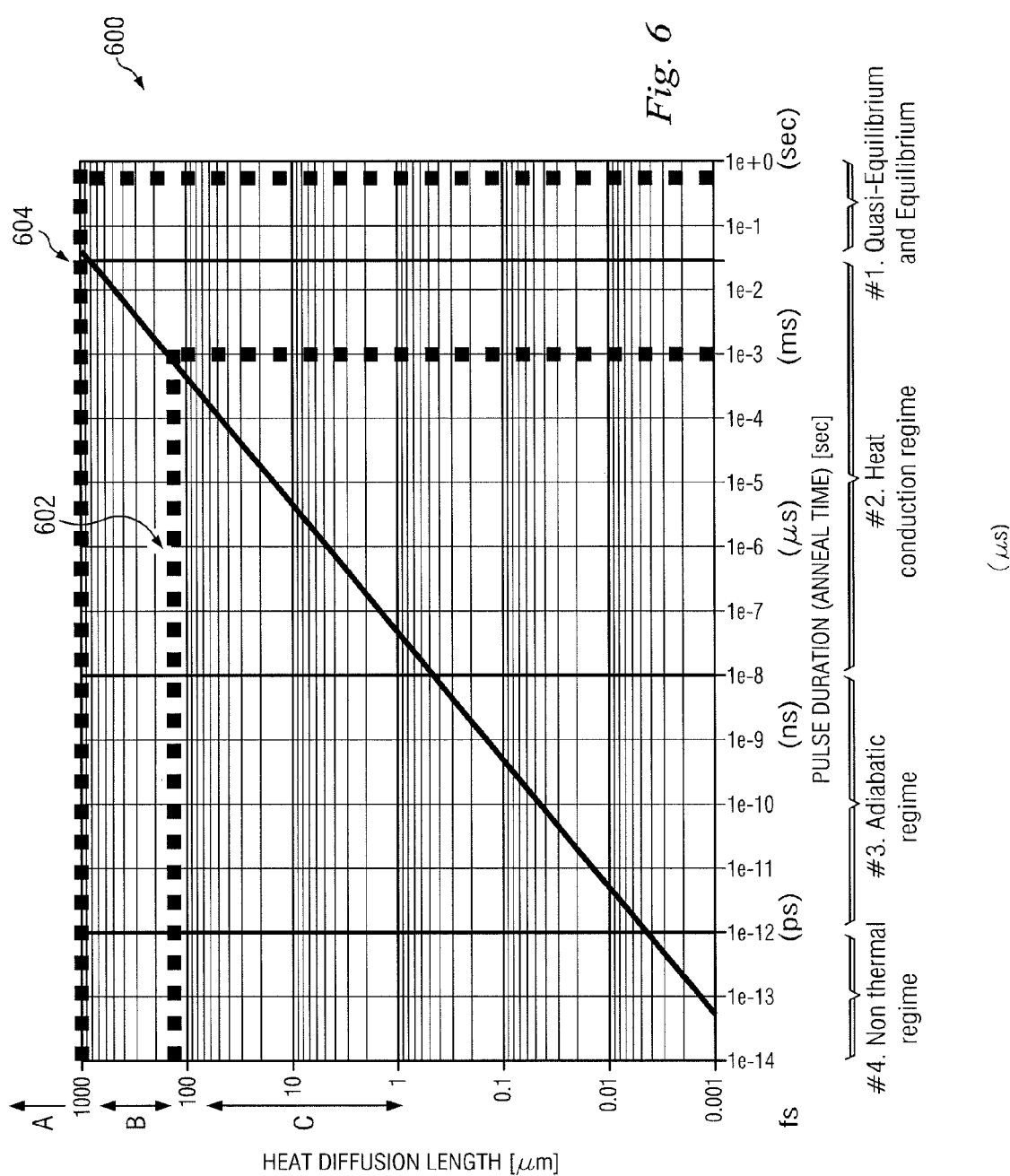
FIG. 6 is a graph illustrating an embodiment of a relationship between pulse duration of an anneal process and a heat diffusion length.

FIG. 6 illustrates a graph 600 providing a semiconductor heating regime. Further description of the graph 600 may be provided in the article P. J. Timans: "A short history of pattern effects in thermal processing," Materials Science Forum Vols. 573-574 (2008) p. 355-374, which is hereby incorporated by reference in its entirety. The graph 600 has an x-axis of pulse duration (anneal time) in seconds. The graph 600 has a y-axis of heat diffusion length in microns ($\mu$m). As described above, for different anneal process techniques, there are different heat diffusion lengths. The graph 600 is illustrative of this principle. For example, the line 602 illustrates a millisecond anneal (mSA) process. The line 604 illustrates a rapid thermal anneal (RTA) process. The graph 600 may be used to determine when a given anneal process will affect the pattern loading effect of the die. In an embodiment, the duration of the anneal process is located on the x-axis and the thermal diffusion length is located on the y-axis for a given anneal process.

In an embodiment, the reflective variation is greater than or equal to 0.1 within a spatial distance of greater than or equal to 1 mm as determined from the reflectivity measurement and/or reflectivity map of the substrate. This provides a spatial distance in region A of the y-axis of graph 600 (greater than 1000 $\mu$m). Thus, in the embodiment, the loading effect will be observed on a micro second anneal, a millisecond flash anneal, a second RTA spike anneal, and any other anneal process having a thermal diffusion length less than region A. In other words, for all anneal processes having a heat diffusion length less than the spatial distance there will be a PLE. Thus, for each of those anneal types, if implemented in the process, implementation of a PLE solution or correction may be desired to avoid and/or mitigate PLE. A PLE solution or correction may include modifications in design (e.g., layout), performance criteria, or modifications of fabrication steps.

In an embodiment, the reflective variation is greater than or equal to 0.1 within a spatial distance between 200 $\mu$m and 1 mm as determined from the reflectivity measurement and/or reflectivity map of the substrate. This provides a spatial distance in region B of the y-axis of graph 600 (between 200 $\mu$m and 1000 $\mu$m). In the embodiment, the loading effect will be observed on a micro second anneal, a millisecond flash anneal, and/or any other anneal process having a thermal diffusion length less than region B. Thus, for each of those anneal types, if implemented in the process, implementation of a PLE solution or correction may be desired to avoid and/or mitigate PLE. In other words, for all anneal processes having a heat diffusion length less than the spatial distance there will be a PLE for which to account. For those anneal types, if implemented in the process, implementation of a PLE solution or correction may be desired to avoid and/or mitigate PLE. In contrast, other anneal types having a larger thermal diffusion length (e.g., a second RTA spike anneal), PLE may not be of concern. In other words, those anneals may be implemented without corrective action.

In an embodiment, the reflective variation is greater than or equal to 0.1 within a spatial distance between 1 µm and 200 µm as determined from the reflectivity measurement and/or reflectivity map of the substrate. This provides a spatial distance in region C of the y-axis of graph 600 (between 1 µm and 200 µm). In the embodiment, the loading effect will be observed on a micro second anneal and/or any other anneal process having a thermal diffusion length less than region C. Thus, for those anneal types, if implemented in the process, implementation of a PLE solution or correction may be desired to avoid and/or mitigate PLE. In other words, for all anneal processes having a heat diffusion length less than the spatial distance there will be a PLE for which to account. In contrast, other anneal types having a larger thermal diffusion length (e.g., a second RTA spike anneal, millisecond flash anneal) may be implemented without necessity of correcting or otherwise addressing PLE.

Thus, the block 110 may include a determination of when an anneal process or anneal process parameter will effect the pattern loading effects of a die or substrate. This determination may include calculating a spatial distance for a given percentage change in reflectivity and comparing this spatial distance to a heat diffusion length associated with the anneal process. A determination can then be made whether the pattern loading effect will be an issue, or not in the process. This may provide for a mechanism by which a determination is made as to what process and/or process parameter to use in the fabrication of the substrate or dies of the same or substantially similar design.

In an embodiment, the block 110 further includes, or alternatively includes, a characterization of the design and/or layout or one or more die on the wafer. The determination associated with the design may include an acceptance of a layout, a determination to modify the layout (e.g., to improve pattern loading effects), a determination to change a material type used in the die, a determination to add a material type or layer, and/or suitable design considerations.

In an embodiment, the block 110 includes a characterization of a device performance parameter associated with one or more die on the substrate. In an embodiment, one or more of the reflectivity map and the thermal map are used to determine (e.g., predict) the device performance parameter(s). In an embodiment, the reflectivity map and/or the thermal map are used to generate a device performance parameter map. The device performance parameter map may be generated using modeling, experimental data, and/or other analysis techniques. The device performance parameter may provide a map of a relative and/or specific value for a given performance parameter of a semiconductor device such as, for example, leakage, speed, delay, and/or other performance metric.

Figure 5:
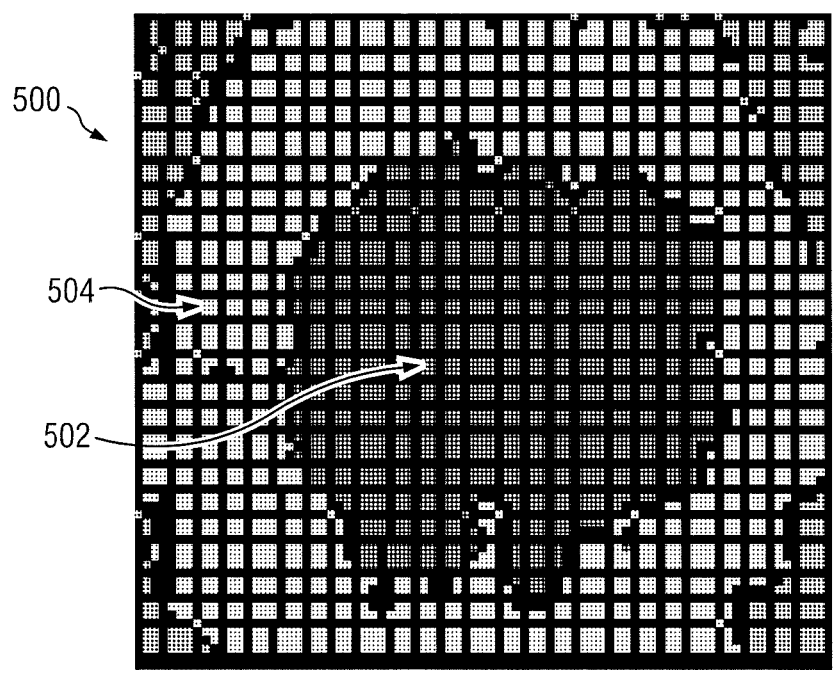
FIG. 5 is an embodiment of a device parameter map, which may be generated in one or more embodiments of the method of FIG. 1.

Referring to the example of FIG. 5, a device performance parameter map 500 is illustrated. The device performance parameter map 500 may be a circuit speed delay map. The device performance parameter map 500 includes a center-region 502 and an edge region 504. The device performance parameter map illustrates a center-slow, edge-fast profile for the associated wafer. In an embodiment, the device performance parameter map 500 may correspond with the thermal map 400, which has a center-hot, edge-cool region. In an embodiment, the device performance parameter map 500 may correspond with the reflectivity map 300, which has a center-low reflectivity, edge-high reflectivity region.

As described above, in block 110 one or more of a process parameter, design, and/or performance parameter characterization for the wafer and/or associated die is determined from at least one of the reflectivity measurement, the reflectivity map, and the thermal map. In an embodiment, the characterization is determined for all wafers having the associated die design. For example, the method 100 may be performed once to characterize a design and/or die and process, design, or performance parameter determinations made may be applied to all the associated die/design.

Thus, the method 100 provides for determination of a suitable process parameter or technique (e.g., an anneal technique or a suitable anneal process parameter) for a given wafer and/or associated design/die. The method 100 may also and/or alternatively provide an analysis of a design (e.g., layout) associated with the wafer, for example, a determination if a desire to mitigate or otherwise account for a pattern loading effect may be provided for by a design change. The method 100 may also or alternatively provide for a determination (e.g., prediction) of a device performance parameter. The characterization of the method 100 may determine whether design changes are required, or the pattern loading effects are not of specific concern. In embodiments, the method 100 may continue to perform subsequent fabrication process including those typical of a CMOS fabrication process. Subsequent processing of the substrate provided in the method 100 may include, for example, forming an inter-layer dielectric (ILD), contacts, inter-metal dielectric (IMD) layers, metallization layers, packaging, and the like.

Figure 7:
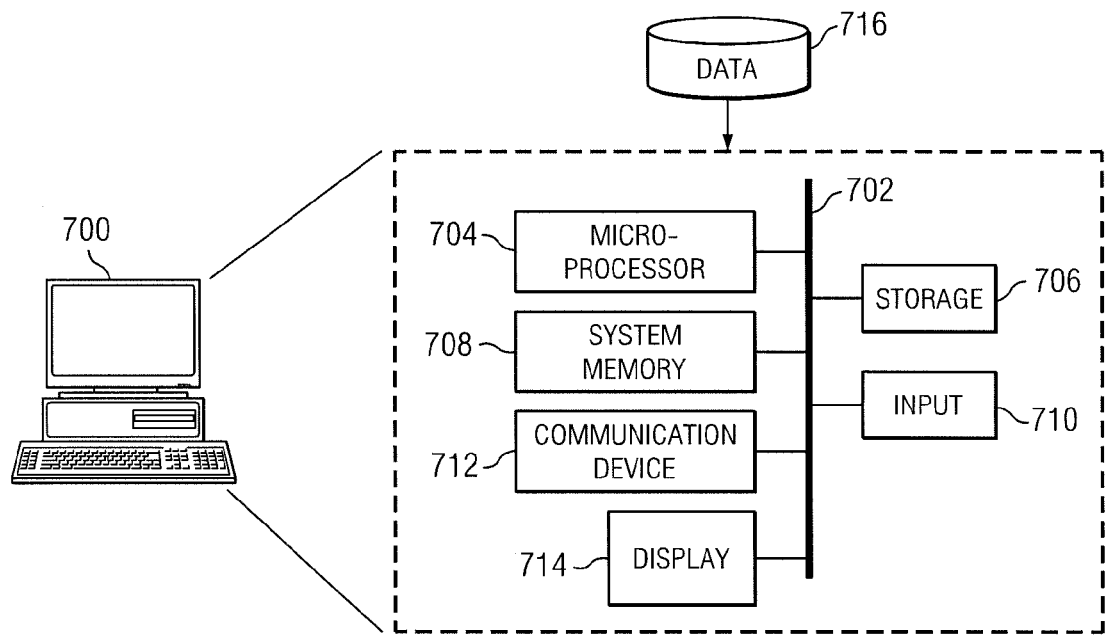
FIG. 7 is a block diagram of an embodiment of a computer system operable to perform one or more steps of the method of FIG. 1.

Referring now to FIG. 7, illustrated is an embodiment of a computer system 700 for implementing embodiments of the present disclosure including the systems and methods described herein. In an embodiment, the computer system 700 includes functionality providing for generation of a reflectivity map, a thermal map, analysis of a reflectivity map, analysis of a thermal map, determination of a process parameter, determination of a design parameter (e.g., layout, material, etc), determination of a concern of a PLE, determination and/or prediction of a device performance parameter (e.g., generation of a device performance parameter) including as described in the method 100 of FIG. 1.

The computer system 700 includes a microprocessor 704, an input device 710, a storage device 706, a system memory 708, a display 714, and a communication device 712 all interconnected by one or more buses 702. The storage device 706 may be a floppy drive, hard drive, CD-ROM, optical device or any other storage device. In addition, the storage device 706 may be capable of receiving a floppy disk, CD-ROM, DVD-ROM, or any other form of computer-readable medium that may contain computer-executable instructions. The communications device 712 may be a modem, a network card, or any other device to enable the computer system to communicate with other nodes. It is understood that any computer system 700 could represent a plurality of interconnected computer systems such as, personal computers, mainframes, PDAs, and telephonic devices. The communications device 712 may allow communications between the computer system 700 and one or more tools or computer systems used in the fabrication and/or testing of an IC.

The computer system 700 includes hardware capable of executing machine-readable instructions as well as the software for executing acts (typically machine-readable instructions) that produce a desired result. Software includes any machine code stored in any memory medium, such as RAM or ROM, and machine code stored on other storage devices (such as floppy disks, flash memory, or a CD ROM, for example). Software may include source or object code, for example. In addition, software encompasses any set of instructions capable of being executed in a client machine or server. Any combination of hardware and software may comprise a computer system. The codes, executed by a computer, may include code for generating reflectivity maps, generating thermal maps, generating process parameter maps, and/or other functionality of the method 100.

Computer readable mediums include passive data storage, such as RAM as well as semi-permanent data storage such as a compact disk read only memory (CD-ROM). In an embodiment of the present disclosure may be embodied in the RAM of a computer to transform a standard computer into a new specific computing machine. Data structures are defined organizations of data that may enable an embodiment of the present disclosure. For example, a data structure may provide an organization of data, or an organization of executable code. Data signals could be carried across transmission mediums and store and transport various data structures, and thus, may be used to transport an embodiment of the present disclosure. The microprocessor 704 may perform the correlation analysis described herein.

The display 714 may be operable to display, in human readable form, for example, the reflectivity map, the thermal map, and/or the device performance parameter map such as exemplified in FIGS. 3, 4, and 5, respectively. A database 716 may be any standard or proprietary database software known in the art. The physical location of the database 716 is not limiting and may exist remotely from the server, be accessible by internet or intranet. The disclosure of the database 716 includes embodiments that include a plurality of databases. The database 716 may include design and/or manufacturing data.

Figure 8:
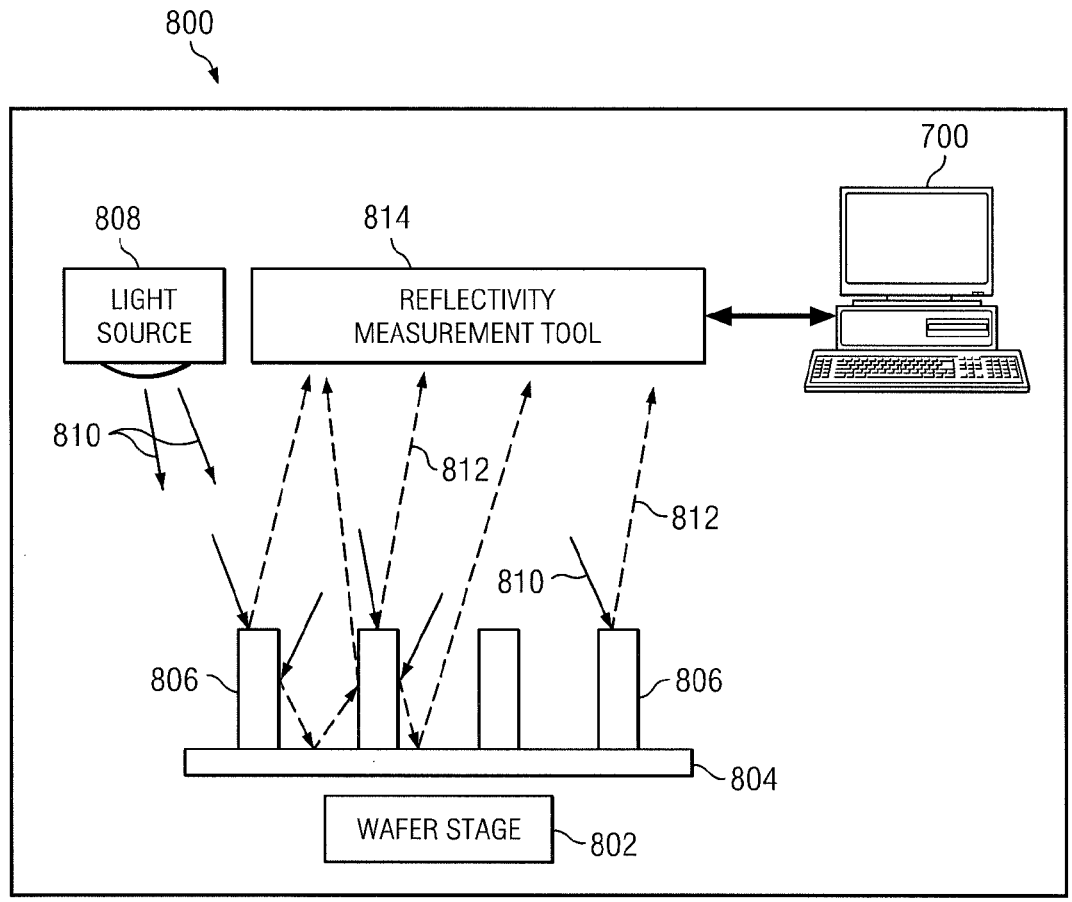
FIG. 8 is a block diagram of a system according to one or more aspects of the present disclosure.

FIG. 8 is a block diagram illustrative of a system 800 that may be used to perform one or more steps of the method 100. The system 800 includes a wafer stage 802 operable to hold a substrate, such as a wafer 804. The wafer may be substantially similar to the wafer described above with reference to block 102 of the method 100 of FIG. 1 and/or the wafer 200, described above with reference to FIG. 2. The wafer 804 includes a pattern 806 formed thereon.

The system 800 further includes a light source 808. The light source 808 may be a source having a relativity short wavelength, such as, for example, a source providing a radiation beam having a wavelength between approximately 200 nanometers (nm) and approximately 750 nm. In an embodiment, a flash Xeon lamp may be used as the light source 808. In an embodiment, the wavelength of the light source 808 is between approximately 300 nm and approximately 500 nm. A spot size of approximately 3 μm may be used. A stepping distance of approximately 50 μm or greater may be used. These parameters are by way of example. The light source 808 provides a radiation 810 directed towards the wafer 804. A portion of the radiation 810 is reflected by the wafer 804, denoted as reflected radiation 812. The amount (e.g., intensity) reflected is dependent upon the pattern 806. One of the light source 808 and the wafer stage 802 may provide for the radiation to be scanned across the substrate.

The system 800 further includes a reflectivity measurement tool 814. The reflectivity measurement tool 814 may provide any means of measuring and/or storing a reflectivity value. The reflectivity value may be determined by the amount of reflected radiation 812. The value determined by the reflectivity measurement tool 814 may be provided to a computer system, such as the computer system 700, described above with reference to FIG. 7.

In summary, the methods and systems disclosed herein provide for thermal induced intra-die (and inter-die) variation characterization. The characterization may include analysis and/or determinations associated with a design, a process parameter, and/or a device performance parameter. For example, the analysis and/or determination may include generation of thermal maps, generation of device performance parameter maps, determination of acceptability of a design/ layout within a given tolerance, determination of a type of anneal process to implement in fabricating devices, and/or other suitable analysis and/or determinations discussed herein. In doing so, various embodiments of the present disclosure may offer several advantages over prior art devices. Advantages of some embodiments of the present disclosure include determination of a design and/or device performance parameters prior to performing an anneal and characterization of a die layout such that it may be used to make processing decisions in subsequent fabrication. Another advantage of an embodiment is that the method and/or system provided may be universal, for example, applicable to various different designs, various different technology nodes, etc. Further, embodiments provide for characterization of on-die variation with a resolution that is smaller than the thermal diffusion length of an anneal process. For example, in an embodiment, the resolution obtained may be 50 μm, which is smaller than the millisecond anneal (mSA) thermal diffusion length. Thus, it is possible to determine and/or resolve mSA induced loading effects. It is understood that different embodiments disclosed herein offer different disclosure, and that one of ordinary skill may make various changes, substitutions and alterations herein without departing from the spirit and scope of the present disclosure.

In the foregoing specification, specific embodiments of the disclosure have been described. However, various modifications and changes can be made by one skilled in the art without departing from the scope of the disclosed embodiments. Accordingly, the specification and figures are to be regarded in an illustrative rather than a restrictive sense, and all such modifications are intended to be included within the scope of the disclosed embodiments.

What is claimed is:

1. A method, comprising:
    performing a reflectivity measurement on a semiconductor wafer, wherein a plurality of reflectivity measurements at different points on the semiconductor wafer are obtained;
    measuring a spatial distance for a reflectivity change using the reflectivity measurement, wherein the spatial distance is a distance across the semiconductor wafer within which the reflectivity change occurs;
    comparing the spatial distance with the thermal diffusion length associated with each of a plurality of anneal process techniques;
    determining an anneal process technique from the plurality of anneal process technique based on the comparison of the spatial distance and the thermal diffusion length; and
    performing the determined anneal process technique on the semiconductor wafer.

2. The method of claim 1, wherein the determined anneal process technique is one of a micro second laser anneal, a millisecond flash anneal, and a rapid thermal anneal (RTA).

3. The method of claim 1, wherein the determined anneal process technique has a thermal diffusion length greater than the spatial distance.

4. The method of claim 1, wherein performing the reflectivity measurement includes performing a scan measurement across the semiconductor wafer.

5. The method of claim 1, wherein the performing the reflectivity measurement includes a performing a plurality of measurements taken at a stepping distance of across the semiconductor wafer, wherein the stepping distance is approximately 50 micrometers or greater.

6. The method of claim 1, wherein the performing the reflectivity measurement includes scanning the semiconductor wafer using a light source providing a radiation having a wavelength between approximately 200 nanometers and approximately 750 nanometers.

7. The method of claim 1, wherein the reflectivity change is approximately 10%.

8. The method of claim 1, further comprising:
providing a reflectivity map using the plurality of reflectivity measurements and wherein the spatial distance is determined by measuring a distance on the reflectivity map over which the reflectivity change occurs.

9. The method of claim 8, further comprising:
generating a thermal map from the reflectivity map.

10. The method of claim 9, further comprising:
generating a process parameter map from at least one of the reflectivity map and the thermal map.

11. The method of claim 10, wherein the process parameter map includes a prediction of a speed of a device.

12. The method of claim 8, wherein the reflectivity map is a two-dimensional representation of at least a portion of the semiconductor wafer.

13. The method of claim 8, wherein the providing the reflectivity map includes plotting the plurality of reflectivity measurements corresponding to a representative sample region of the semiconductor wafer.

14. A method, comprising:
performing a reflectivity measurement on a semiconductor wafer;
generating a reflectivity map based on the received reflectivity measurement, wherein the reflectivity map indicates a reflectivity corresponding to a plurality of points on the semiconductor wafer;
selecting a reflectivity change amount, wherein the reflectivity change amount is a percentage;
determining a spatial distance within which the selected reflectivity change is provided by using the generated reflectivity map, wherein the spatial distance corresponds to a length of a surface of the semiconductor wafer, wherein reflectivity within the length varies by the percentage;
comparing the determined spatial distance with a thermal diffusion length of a first anneal process technique to select a specified anneal process; and
performing the specified process technique on the semiconductor wafer.

15. The method of claim 14, further comprising:
comparing the determined spatial distance with a thermal diffusion length of a second anneal process technique.

16. The method of claim 15, further comprising:
selecting the second anneal process technique as the specified anneal process based on a pattern loading effect.

17. The method of claim 15, further comprising:
if the determined spatial distance is less than the thermal diffusion length of the first anneal process technique;
then selecting the first anneal process technique as the specified anneal process.

18. The method of claim 14, further comprising:
generating a device performance parameter map from the reflectivity map.

19. The method of claim 14, further comprising:
generating a thermal profile map from the reflectivity map.

20. The method of claim 14, wherein the percentage is approximately 10.

* * * * *